(12) United States Patent
Izmailov et al.

(10) Patent No.: US 9,476,826 B2
(45) Date of Patent: Oct. 25, 2016

(54) SIGNAL AND DETECTION SYSTEM FOR KEYING APPLICATIONS

(71) Applicant: Smart Wave Technologies Corp., Toronto, Ontario (CA)

(72) Inventors: Alexandre Izmailov, Etobicoke (CA); Peter Zosimadis, Brampton (CA)

(73) Assignee: Smart Wave Technologies Corp., Toronto (CA)

( * ) Notice: Subject to any disclaimer, the term of this patent is extended or adjusted under 35 U.S.C. 154(b) by 0 days.

(21) Appl. No.: 13/791,073

(22) Filed: Mar. 8, 2013

(65) Prior Publication Data

US 2013/0188187 A1 Jul. 25, 2013

Related U.S. Application Data

(63) Continuation of application No. PCT/CA2011/001008, filed on Sep. 9, 2011.

(60) Provisional application No. 61/381,671, filed on Sep. 10, 2010.

(51) Int. Cl.
| | |
|---|---|
| *G01J 3/46* | (2006.01) |
| *G01N 21/27* | (2006.01) |
| *B44F 1/02* | (2006.01) |
| *G01N 21/55* | (2014.01) |
| *G01N 21/84* | (2006.01) |
| *G07D 7/12* | (2016.01) |

(Continued)

(52) U.S. Cl.
CPC ............... *G01N 21/27* (2013.01); *B44F 1/02* (2013.01); *G01N 21/251* (2013.01); *G01N 21/55* (2013.01); *G01N 21/8422* (2013.01); *G07D 7/122* (2013.01); *A47K 5/1217* (2013.01); *G01N 21/256* (2013.01); *G01N 2021/8427* (2013.01)

(58) Field of Classification Search
CPC .. G07F 7/086; G01N 21/8422; G01N 21/55; G01N 2035/00752; G01N 35/00732; B41M 3/14; A47K 5/1217; B01F 13/1055
See application file for complete search history.

(56) References Cited

U.S. PATENT DOCUMENTS

| | | | |
|---|---|---|---|
| 4,204,765 A | | 5/1980 | Iannadrea et al. |
| 4,568,141 A | * | 2/1986 | Antes ............ G02B 5/1842 283/904 |
| 5,093,147 A | | 3/1992 | Andrus et al. |

(Continued)

FOREIGN PATENT DOCUMENTS

| | | |
|---|---|---|
| JP | 11342662 A | 12/1999 |
| JP | 2003521050 A | 7/2003 |

(Continued)

OTHER PUBLICATIONS

International Search Report Application No. PCT/CA2011/001008 Completed: Nov. 3, 2011; Mailing Date: Nov. 16, 2011 2 pages.

(Continued)

*Primary Examiner* — Kara E Geisel
*Assistant Examiner* — Maurice Smith
(74) *Attorney, Agent, or Firm* — Whitmyer IP Group LLC

(57) ABSTRACT

Systems and methods for differentiating the spectral response of various optical coatings between a transmitter and receiver. The system is effective in determining if an optical coating produces an authorized spectral response for determining if a product having that optical coating is authorized to be used with another product.

24 Claims, 7 Drawing Sheets

(51) Int. Cl.
*G01N 21/25* (2006.01)
*A47K 5/12* (2006.01)

(56) References Cited

U.S. PATENT DOCUMENTS

| | | | | |
|---|---|---|---|---|
| 5,114,226 | A * | 5/1992 | Goodwin | G01S 7/4812 250/206.2 |
| 5,856,048 | A * | 1/1999 | Tahara | B41M 3/14 283/85 |
| 5,862,844 | A | 1/1999 | Perrin | |
| 6,045,894 | A * | 4/2000 | Jonza | B32B 27/36 428/141 |
| 6,234,537 | B1 | 5/2001 | Gutmann et al. | |
| 6,458,294 | B2 | 10/2002 | Oshima et al. | |
| 6,793,723 | B2 | 9/2004 | Auslander et al. | |
| 6,899,752 | B2 | 5/2005 | Sekioka et al. | |
| 7,040,566 | B1 | 5/2006 | Rodrian et al. | |
| 7,097,074 | B2 | 8/2006 | Halliday et al. | |
| 7,192,474 | B2 | 3/2007 | Auslander et al. | |
| 7,621,426 | B2 | 11/2009 | Reynolds et al. | |
| 7,630,109 | B2 * | 12/2009 | Phillips | B42D 25/328 283/91 |
| 2003/0042438 | A1 * | 3/2003 | Lawandy et al. | 250/556 |
| 2003/0126019 | A1 * | 7/2003 | Taylor | G06Q 20/202 705/21 |
| 2005/0145745 | A1 | 7/2005 | Lewis et al. | |
| 2005/0217969 | A1 | 10/2005 | Coombs et al. | |
| 2006/0058724 | A1 * | 3/2006 | Handfield | A61J 7/0084 604/20 |
| 2006/0092210 | A1 | 5/2006 | Maniam et al. | |
| 2006/0097514 | A1 | 5/2006 | Nishimura et al. | |
| 2006/0124741 | A1 * | 6/2006 | Mayer et al. | 235/454 |
| 2006/0180792 | A1 | 8/2006 | Ricci et al. | |
| 2008/0087189 | A1 | 4/2008 | Lin et al. | |
| 2008/0087190 | A1 | 4/2008 | Iftime et al. | |
| 2008/0274028 | A1 | 11/2008 | Lin et al. | |
| 2009/0051158 | A1 * | 2/2009 | Scholz et al. | 283/92 |
| 2009/0109682 | A1 | 4/2009 | Gardner et al. | |
| 2009/0159510 | A1 | 6/2009 | Haushalter et al. | |
| 2009/0177315 | A1 | 7/2009 | Goeking et al. | |
| 2009/0276091 | A1 | 11/2009 | Duha et al. | |
| 2010/0036528 | A1 | 2/2010 | Minard et al. | |
| 2010/0147879 | A1 | 6/2010 | Ophardt et al. | |

FOREIGN PATENT DOCUMENTS

| | | |
|---|---|---|
| JP | 2003260804 A | 9/2003 |
| JP | 2005022292 A | 1/2005 |
| WO | 9016043 A1 | 12/1990 |

OTHER PUBLICATIONS

Office Action from Canadian Intellectual Property Office Application No. 2,810,701 Issued: Oct. 15, 2014 4 pages.

Second Office Action from China Application No. 201180043524.3 Apr. 21, 2015 5 pages (translation included).

Extended European Search Report and Opinion Application No. EP 11 82 2955 Completed: Mar. 13, 2015; Mailing Date: Mar. 23, 2015 8 pages.

Office Action from Japan Application No. 2013-527428 Jul. 15, 2015 7 pages.

Japanese Office Action Application No. 2013-527428 Issued: Apr. 5, 2016 7 pages.

* cited by examiner

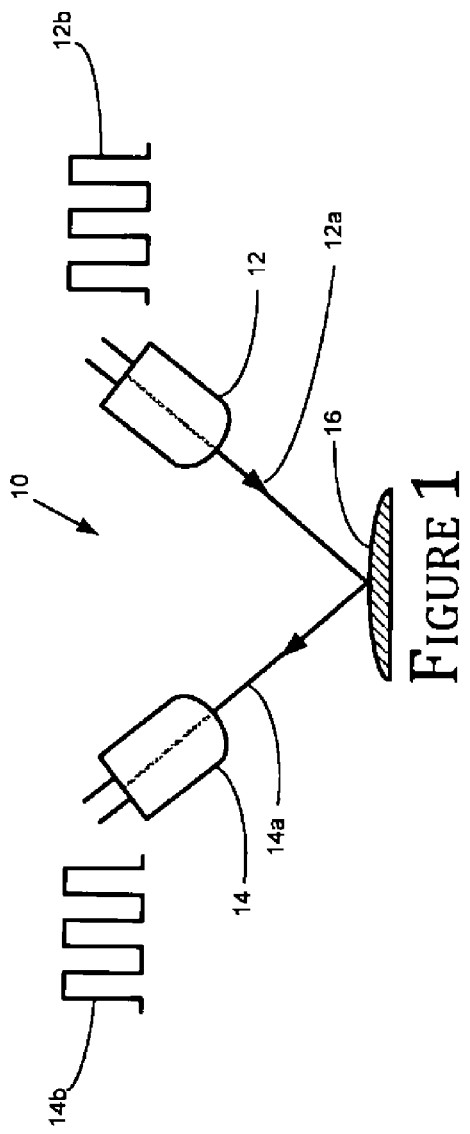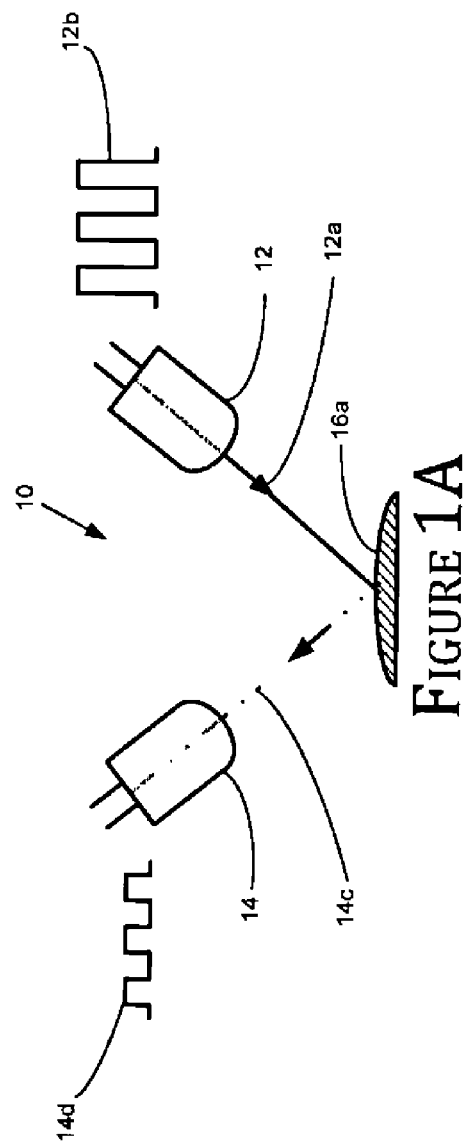

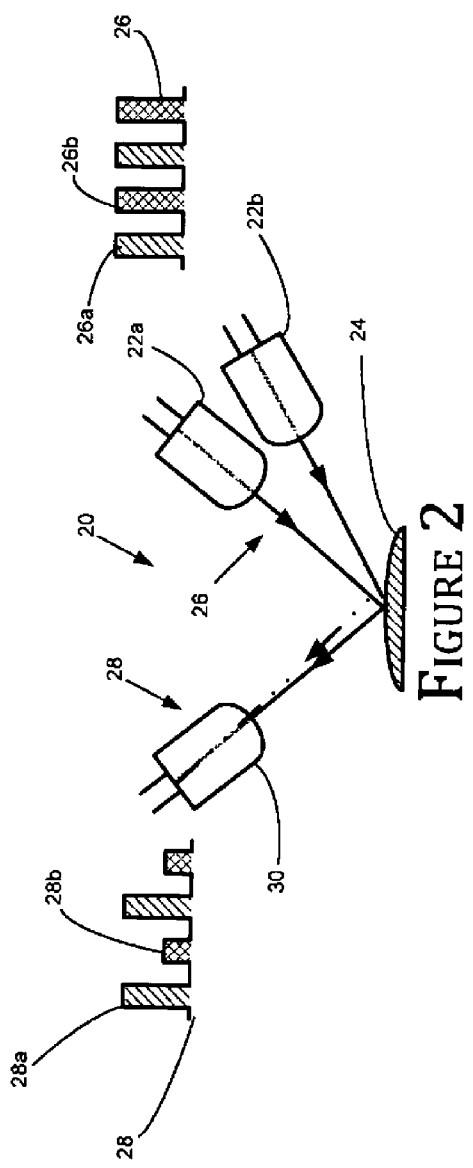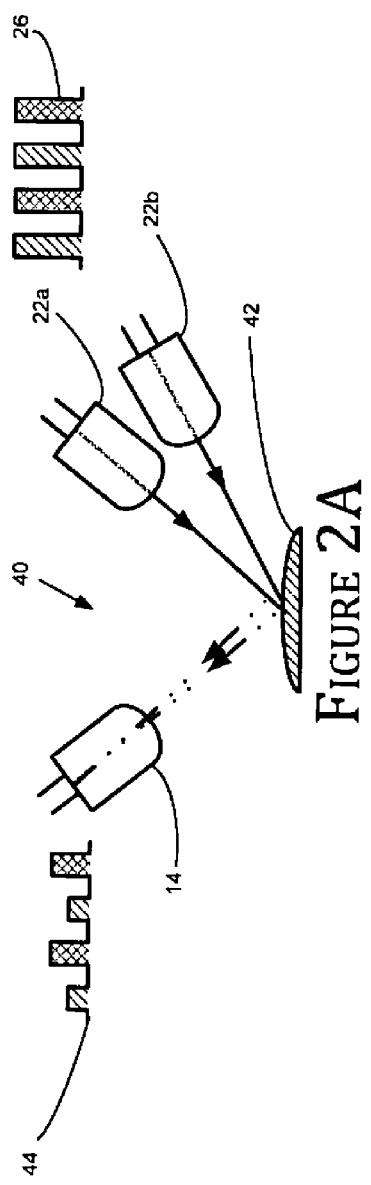
FIGURE 2
FIGURE 2A

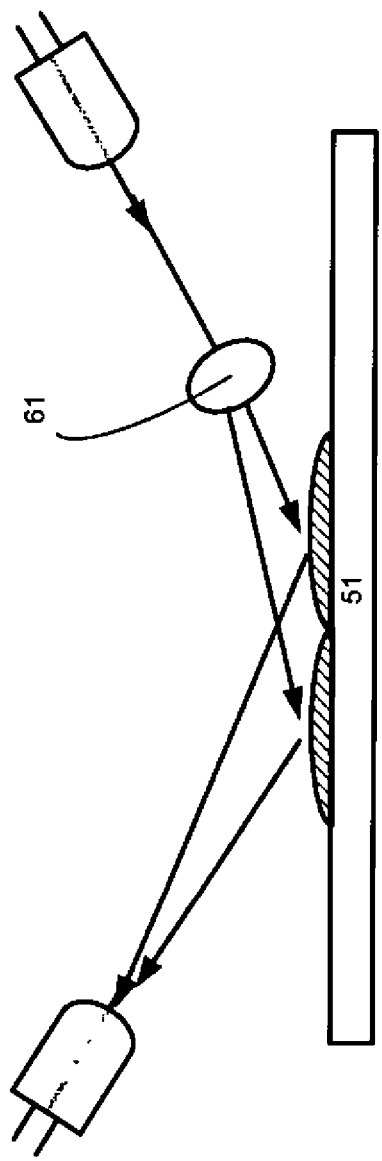

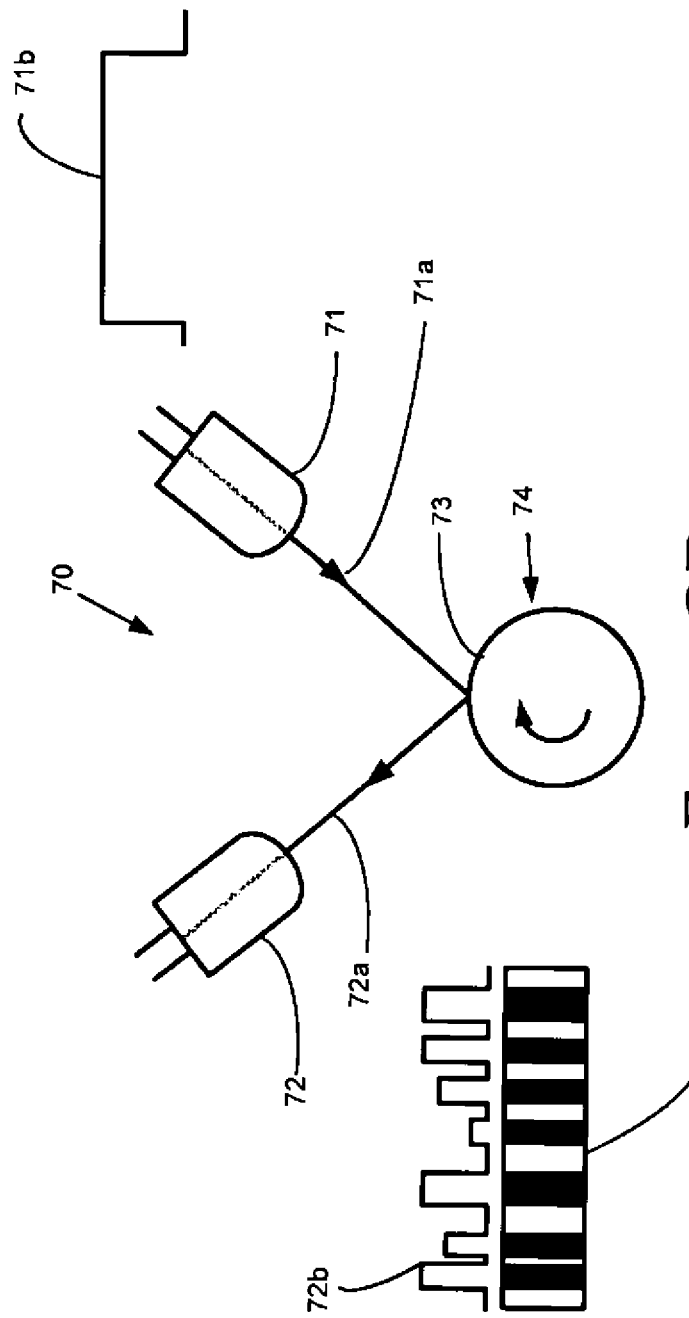

SIGNAL AND DETECTION SYSTEM FOR KEYING APPLICATIONS

FIELD OF THE INVENTION

Systems and methods for differentiating the spectral response of various optical coatings between a transmitter and receiver are described. The systems and methods are effective in determining if an optical coating produces an authorized spectral response that can be used in a number of applications including determining if a product having that optical coating is authorized to be used with another product.

BACKGROUND OF THE INVENTION

In today's competitive marketplace, the costs for companies to create, maintain and grow new markets and market share is becoming increasingly expensive. As such, there is an increasing demand for technologies that provide a low cost means of ensuring that a company's (a "first company") investment into a product and/or marketplace is protected against newcomers that may be attempting to get into that marketplace by following the lead of the first company. That is, there exists a need for companies to have a means of protecting the products they develop from being counterfeited and/or being undercut by newcomers who, by utilizing the research and development of the first company, can produce a counterfeit or cheaper product without the same degree of development work. In addition, it is also very important for the first company, who may also have invested substantially in the brand name and/or goodwill associated with a product to protect the brand name and/or goodwill and the associated revenue stream by reducing the ability of competitors to create and market products that provide similar or confusingly similar products that can be used with the first company's products.

The above is particularly important for companies selling consumable products and the case where a competitor may wish to sell a competing "re-fill" type product for use with a particular apparatus of the first company. For example, the first company may have developed a dispensing product that includes a dispensing apparatus that incorporates a consumable component in the form of a cartridge or other container. In this case, the consumable component is replaced at regular intervals after the consumable is used up and the first company looks to re-coop its development costs for the dispensing apparatus through the repeated sales of the consumable component. Often, a competitor will seek to undercut the pricing of the consumable component by producing an "unauthorized" consumable component that can be used with the first company's dispensing product without incurring the development costs of either the more expensive dispensing product and/or the consumable component. In the past, while there have been various solutions developed to make it more difficult for the competitor to successfully integrate an unauthorized consumable product with various dispensing apparatus, there continues to be a particular need for lower cost solutions that prevent the use of unauthorized products within certain apparatus in order to protect the brand name and/or revenue stream of the authorized product. In addition, a lower cost solution may expand the number of products in which an authentication process could be implemented between the different product pairs.

Past systems have included a variety of technologies that provide primary product/consumable product matching that limits or prevents the ability to use unauthorized consumable products with a primary product. Such technologies have included bar code systems, radio frequency identification systems and the like. While each of these technologies can be effective, as noted above, there continues to be a need for technologies providing a lower cost solution.

A review of the prior art indicates that the use of light-emitting diode (LED) transmitters and receivers have not been used in the past as a means for providing keying between primary product/consumable product pairs.

For example, US Patent Publication 2009/0177315 (Goeking) discloses a method of dispensing authorized product loaded into a dispenser by optically identifying a reference indication associated with the product. The reference indications include one or more marks that phosphorescence when in the presence of light from a light source.

US Patent Publication 2010/0147879 (Ophardt) discloses a replaceable keying component which includes a waveguide having a photochromic portion. Operation involves the input of electromagnetic radiation through one end of the waveguide and detecting electromagnetic radiation at the output of the waveguide to determine if the material contains one or more compatible photochromic compounds.

US Patent Publication 2010/0036528 (Minard) discloses a dispenser utilizing a control system that receives package-specific information via an optical scanner or a radio frequency sensor. The radio frequency sensor is included in a data input system employing radio frequency identification (RFID) technology. Radio scanners receive and analyze the radio signals emitted by an RFID tag.

U.S. Pat. No. 5,862,844 (Perrin) discloses a system for controlling a dispensing apparatus with one or more illumination sources and one or more optical sensors along with a control circuit. The control circuit responds to at least one of the optical sensors to initiate dispensing of the material. The control circuit is designed to actuate a dispensing appliance from above when a container is presented directly below an outlet.

U.S. Pat. No. 7,621,426 (Reynolds) discloses a system for dispensing product by utilizing an electronically powered key device and/or identification code from an authenticated refill container. The system utilizes a near field frequency response to determine the compatibility of the refill container.

US Patent Publication 2009/0276091 (Duha) discloses an apparatus for analyzing readable tags to ensure the use of authenticated paint in paint dispensers.

SUMMARY OF THE INVENTION

In accordance with the invention, systems and methods for differentiating the spectral response of various optical coatings between a transmitter and receiver are described. The systems described herein are effective in determining if an optical coating produces an authorized spectral response for then determining if a product having that optical coating is authorized to be used with another product.

In accordance with a first aspect, there is provided a system for differentiating the spectral response of one or more optical coatings on a substrate between a transmitter and receiver comprising: a transmitter operatively located adjacent the optical coating for transmitting a first light signal against an optical coating; a receiver operatively located adjacent the optical coating for receiving reflected light off the optical coating; and, receiver electronics operatively connected to the receiver for interpreting reflected light at the receiver against an authorized signal and determining if the optical coating is an authorized or unauthorized optical coating. In a preferred embodiment, the transmitter is an LED light source.

In another embodiment the system includes at least two transmitters and each transmitter transmits a different wavelength of light against the optical coating.

In one embodiment, the transmitter transmits light against a common optical coating and the optical coating has different reflection properties to each wavelength of light.

In another embodiment, the authorized signal is a combination of received signals from each transmitter.

In yet another embodiment, the optical coating includes at least two optical coatings and each optical coating is paired with a corresponding transmitter and receiver pair.

In another embodiment, each transmitter of each transmitter and receiver pair emits different wavelength light. The at least two optical coatings may also have different reflective properties.

In another embodiment, the optical coating includes at least two spatially distinct optical coatings and a single transmitter and receiver pair and wherein light from the transmitter is diverted through an optical system to each of the at least two spatially distinct optical coatings and reflected light from each of the at least two spatially distinct optical coatings is received in the receiver of the transmitter and receiver pair.

In one embodiment, each of the at least two spatially distinct optical coatings has different reflection properties.

In yet another embodiment, the substrate is a rotating substrate and the rotating substrate includes at least one optical coating that rotates past a reflection point of the transmitter and receiver pair on the substrate. The substrate may also include at least two optical coatings that have different reflection properties.

In one embodiment, the at least two optical coatings have substantially the same color and different reflection properties.

In another embodiment, the LED is a multi-color LED enabling sequenced generation of at least two wavelengths within the LED and wherein the receiver receives a corresponding reflected signal of the at least two wavelengths.

In another embodiment, the input light signal(s) is/are pulsed.

In another aspect, the invention provides a system for differentiating the spectral response of at least two optical coatings on a substrate comprising at least one transmitter and receiver pair including a transmitter and a receiver, the transmitter for transmitting a light signal against first and second optical coatings on the substrate, the system including an optical element positioned adjacent the transmitter for diverting a portion of the light signal against the second optical coating, wherein the receiver is operatively located adjacent the first and second optical coating for receiving reflected light off the first and second optical coatings.

In yet another aspect, the invention provides a method of evaluating a substrate having an optical coating in relation to a primary apparatus comprising the steps of: a) positioning the optical coating of the substrate in an operative position relative to the primary apparatus; b) transmitting a first light signal against the optical coating from the primary apparatus; c) receiving a reflected light signal on the primary apparatus from light reflected off the optical coating; d) comparing the reflected light signal to a pre-determined signal pattern and determining if the reflected light signal matches the pre-determined signal pattern; e) providing a response signal based on the result of step d).

In another embodiment, step b) includes at least a second light signal.

In yet another embodiment, the optical coating is at least two optical coatings and wherein each optical coating is paired with a corresponding transmitter and receiver pair such that steps a)-c) includes positioning, transmitting and receiving across corresponding transmitter and receiver pairs.

In yet another embodiment, each of the at least two optical coatings has different reflection properties.

BRIEF DESCRIPTION OF THE DRAWINGS

The invention is described with reference to the accompanying figures in which:

FIG. 1 is a sketch of a keying system in accordance with a first embodiment of the invention with an authorized optical coating;

FIG. 1A is a sketch of a keying system in accordance with a first embodiment of the invention with an un-authorized optical coating;

FIG. 2 is a sketch of a keying system in accordance with a second embodiment of the invention with an authorized optical coating;

FIG. 2A is a sketch of a keying system in accordance with a second embodiment of the invention with an un-authorized optical coating;

FIG. 3A is a sketch of a keying system in accordance with one embodiment of the invention having optics enabling a single transmitter/receiver pair to be used with two distinct optical coatings;

FIG. 3B is a sketch of a keying system in accordance with one embodiment of the invention having a rotating substrate enabling a more complex code to be paired with a single transmitter/receiver;

DETAILED DESCRIPTION OF THE INVENTION

Figure 3:
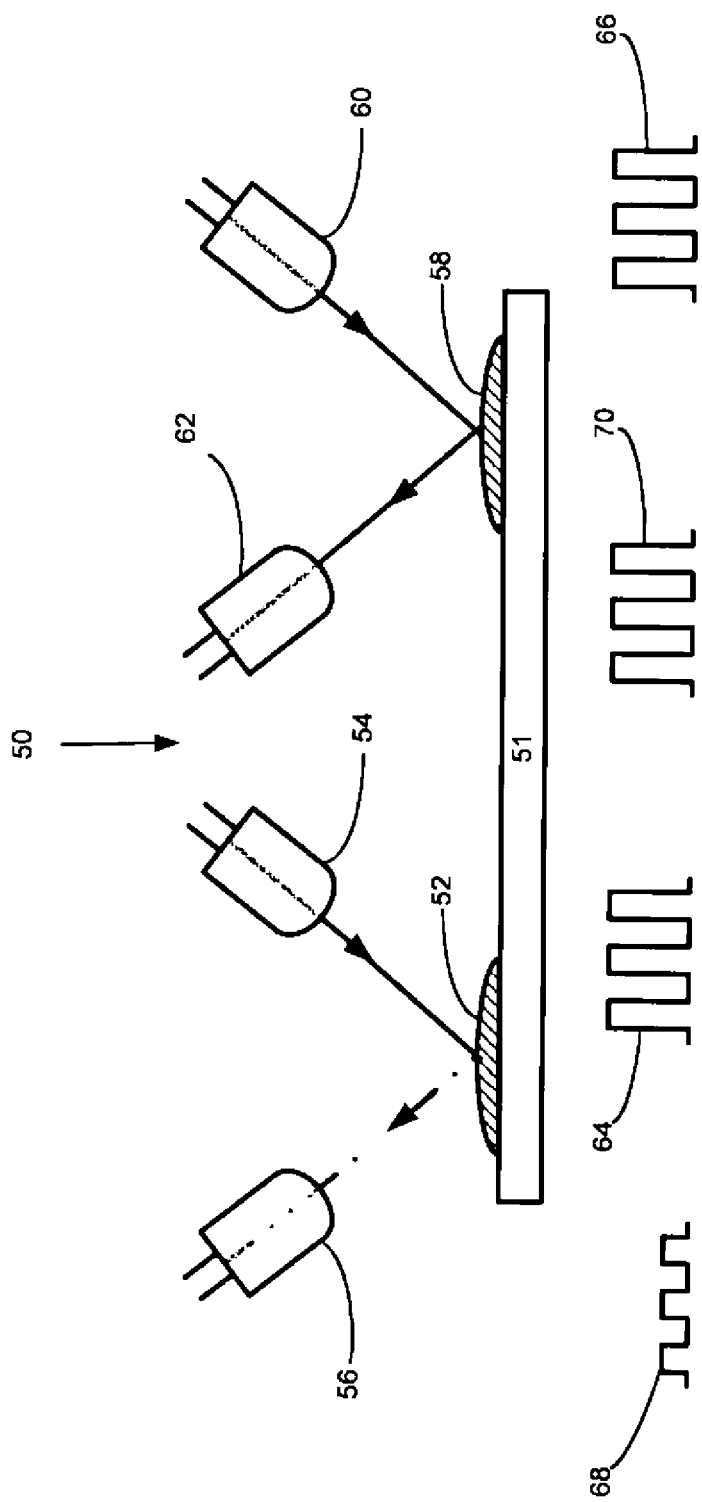
FIG. 3 is a sketch of a keying system in accordance with a third embodiment of the invention with an authorized optical coating.

With reference to the figures, signal and detection systems for keying applications are described in which the reflectivity properties of various optical coatings including but not limited to inks, paints, pigments, and dyes are used to signal if an item on which the optical coating is placed is an authorized item or not. The system is described with reference to various examples in which underlying concepts of operation are described. As explained in greater detail, the concepts described herein may be used in different embodiments and applications in order to achieve the objectives of the invention.

In more specific aspects, the invention describes the use of one or more LED transmitters, receivers and optical coatings including paints that can deployed in a number of configurations for keying applications. These embodiments utilize the absorption and reflection properties of the optical coatings allowing for the analysis of spectral responses. By combining one or multiple LED light sources with one or more optical coatings, a reflected signal pattern may be comprised of a variety of spectral features that can be used to define a specific authorized signal pattern.

Importantly, the subject system can provide a number of advantages over other systems including lower power levels to achieve keying as well as lower material costs generally by using reflectance instead of fluorescence or phosphorescence for labelling or keying purposes.

In the context of this invention, any number of codes between two related products can potentially be established using the principles described herein that can be used by manufacturers/users to signal a wide number of meanings and initiate various actions. Similarly, the electronics used in signal generation and signal interpretation and any subsequent actions that associated electronics may initiate are highly variable but readily integrated to the technology described herein as understood by those skilled in the art.

In accordance with the invention and as shown in FIGS. 1A and 1B, in a first embodiment, a system 10 includes a transmitter 12 and a receiver 14. Generally, the transmitter emits light of a particular wavelength against an optical coating 16 whereupon the light is reflected towards a receiver 14. Based on the properties of the optical coating 16 (see FIG. 5), the signal received at the receiver will vary as a result of the degree of reflection and/or absorbance of light at the optical coating. By way of example, in FIG. 1, the transmitter emits a yellow beam of light 12a and the optical coating 16 has been engineered to reflect yellow light such that the transmitted signal 12a is substantially the same as received signal 14a at the receiver as shown by the solid line. A representative signal pattern for the transmitted and received signals are shown as signals 12b, 14b in which the both the wavelength and signal strength are shown to be substantially identical.

In contrast, as shown in FIG. 1A, if the optical coating 16a has properties that absorb yellow light, then the received signal 14c, 14d will be representative of the yellow light being absorbed by the optical coating. The partially absorbed signal is shown by the dotted line. Similarly, if transmitter 12 is changed to emit red light while the optical coating is designed to reflect yellow light a different received signal will be observed.

As a result, by altering the color of the transmitted light and/or the optical coating, and monitoring the reflection off the optical coating, the relative differences or similarities in spectral reflectivity, can be used to determine if the optical coating is authorized or not as may be interpreted by associated electronics. Thus, if the optical coatings are applied to products, the technology can be used to create coded information that can effectively allow or prevent the use of one product with another product (or other functions) when paired with the appropriate electronics.

In addition, the basic concepts described above can be expanded to create more complex signal responses and, hence, the relative degree of complexity in coding between two products as explained in greater detail below.

As shown in FIGS. 2, 2A, and 3, the system can be expanded to include illumination using more than one light sources and/or optical coating to allow for more complex system responses.

With reference to FIG. 2, a configuration 20 is described having two transmitters 22a, 22b in which transmitter 22a emits light of one color (e.g. orange) and transmitter 22b emits infra-red. In this case, the optical coating 24 is reflective of orange light but not infra-red. As shown, the transmission signal 26 may comprise alternate pulses of orange 26a and infra-red 26b such that the received signal 28 is comprised of higher intensity 28a (corresponding to the orange light received) and lower 28b intensity (corresponding to the infra-red light) signals received at receiver 30. In this case, the alternating high and low intensity signals may be indicative of an authorized optical coating.

In comparison, as shown in FIG. 2A, a non-authorized optical coating 42 may absorb orange light and be partially reflective of infra-red resulting in a received signal 44 that does not match the authorized signal pattern. As such, the associated electronics would not recognize this signal as an authorized signal.

As shown in FIG. 3, a further combination 50 is described. In this case, distinct optical coatings on the same substrate 51 are provided with distinct transmitter and receiver pairs. A first optical coating 52 is paired with a first transmitter 54 and first receiver 56 and a second optical coating 58 is paired with a second transmitter 60 and second receiver 62. In this example, transmitters 54 and 60 emit the same light against different optical coatings 52 and 58 such that 64 and 66 transmit signals are identical but received signals 68 and 70 are different. As a result, the associated electronics would determine if the signals received for both transmitter/receiver pairs matched the authorized signal.

Importantly, the color and appearance of optical coatings can appear substantially identical to the naked eye such that in the absence of relatively sophisticated equipment, it becomes difficult for persons attempting to replicate the optical coating to do so. Moreover, as is understood by those skilled in the art, relatively minor differences in optical coating chemistry and the physical separation/positioning of the optical coatings can be sufficient to substantially alter the spectral response such that replication or duplication of the optical coating can be difficult.

In further examples, other combinations can be utilized. For example, systems can incorporate a greater number of transmitters against a single optical coating, different transmitters against spatially separated optical coatings and/or a different number of receivers. In other embodiments, duplicate transmitter and receiver systems could be employed in which both received signals would have to match within a threshold value to ensure authorization.

Figure 4:
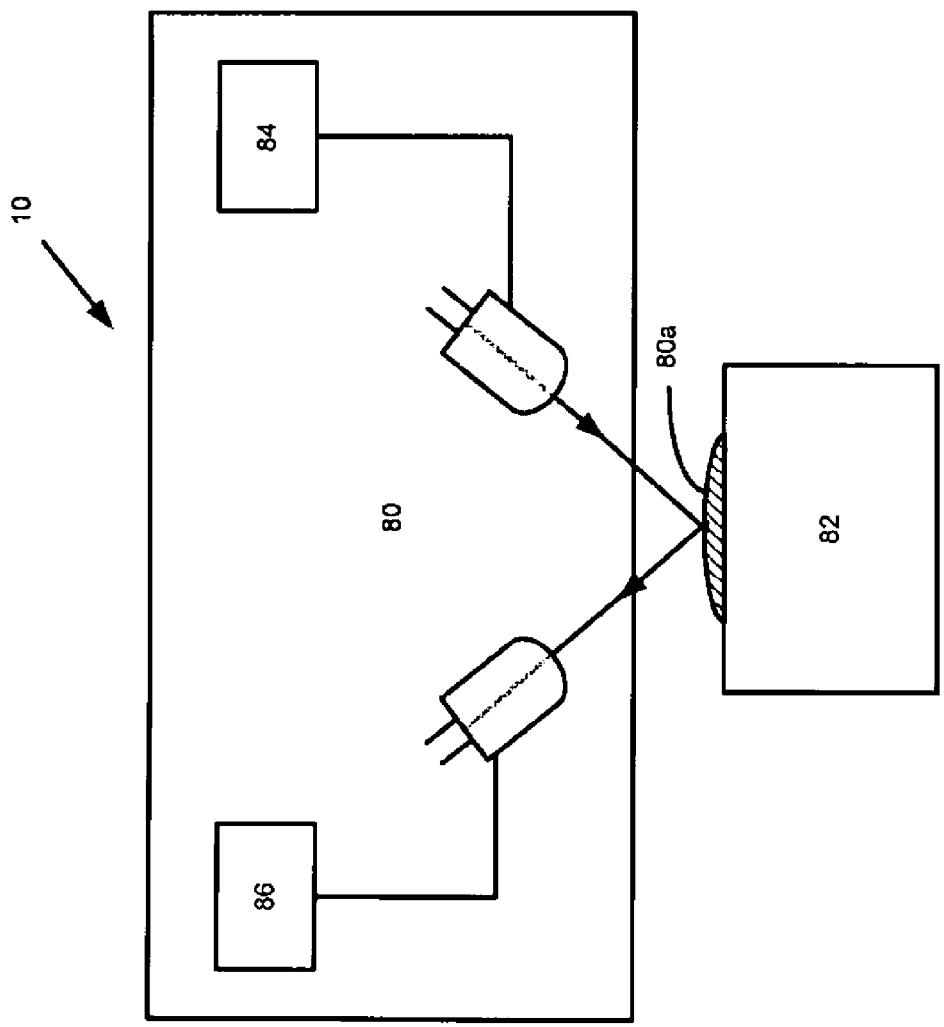
FIG. 4 is a sketch of a keying system in accordance with one embodiment of the invention as a product pair; and, FIG. 5 is a spectral reflection profile for a representative paint showing three possible wavelengths that could be used in an embodiment of the invention.

FIG. 4 shows a representative deployment of the system in which a first product 80 is paired with a second product 82. As shown, the first product includes electronics 84 to provide a transmit signal and receiver electronics 86 to receive and interpret the receive signal in order to determine if the optical coating 80a on second product 82, and hence second product 82 is authorized for use with first product 80. As noted above, electronics 84 and receiver electronics 86 can be designed to provide a wide variety of functions as understood by those skilled in the art.

EXAMPLES

Example 1

Signal Strength

Signal strength experiments were conducted to determine the voltage response of reflected LED light against a reflective paint substrate. An LED (3.5V; 5 mA) was positioned adjacent a reflective paint containing 10C873 pigment (Shepard Color Company). Reflected light was received by a light-to-voltage (LTV) converter (TS252 with a 10 kΩ load) having an integrated lens and optimized for a visible light and near IR response. A 3.5 V signal was received by the LTV convertor thereby demonstrating that a significant signal can be received at the LTV.

Example 2

LED Sensor Module

A photodiode (Hamamatsu S2386-18L) having a similar spectral sensitivity to the photodiode of example 1 was tested with 410 and 680 nm and 430 and 650 nm LEDs respectively. The photodiode showed significant signal can be received at the photodiode.

Example 3

Use of Two Paints Having Similar Appearance But Different Reflecting Characteristics Two black paints, black 30C591 and black 20F944 (Shepard Color Company) were deposited on a substrate in a side-by-side alignment and illuminated using a 950 nm LED. The received signal at the LTV was measured at 3.25 V with Black 30C591 and 1.25V with Black 20F944 thus indicating that substrates having substantially similar colors can provide a distinct reflectivity pattern from different regions of a coated substrate with a fixed input wavelength of light.

Example 4

Two Color Illumination

Paints having an uneven spectral curve of reflectivity were illuminated with two distinct wavelengths and the reflected signals were compared. Brown 10C873 (Shepard Color Company) was illuminated with orange LED light (595 nm) and IR LED light (950 nm). A TSL 252 photosensor was used to detect reflected light. The results showed that 595 nm light produced almost no reflected signal whereas the 950 nm light produced a significant reflected signal. These results showed that a single paint can provide a distinct reflectivity pattern from different LED light sources.

In a second experiment, Yellow 10P270 pigment (Shepard Color Company) was illuminated with a blue LED (470 nm) and red LED (650 nm). The results indicated that reflection at 640 nm was approximately 6 fold higher than reflection at 470 nm.

In this experiment, a control substrate (paper surface having no paint) was compared to the painted test substrates and revealed that the reflectivity of the unpainted substrate at both 470 nm and 650 nm was substantially similar (±5%).

Example 5

Rotating Substrate

With reference to FIG. 3B, one embodiment 70 of the keying system is described in which the substrate is incorporated onto a rotating surface 73 with a transmitter 71 and receiver 72 positioned to transmit 71a and receive 72a light to and from the rotating surface. Importantly, this embodiment allows significantly more complex codes to be incorporated with the substrate without the need or complexity of additional transmitter/receiver pairs. For example, the substrate may include a plurality of stripes 74 on the outer or inner surface of the rotating substrate such that each stripe will pass the reflection point of the transmitter/receiver pair as the substrate rotates. Thus, as can be understood, the relative complexity of codes that can be incorporated onto a rotating substrate can be substantially increased by varying such parameters as the paint (i.e. type) of the stripes, the width of stripes and/or the shape of the substrate. As a representative example, FIG. 3B shows an input signal 71 that based on the properties of the stripes may produce a received signal 72b having the profile characteristics as shown. In this example, both the width of the stripes and the paint types has been varied to produce the authorized signal that is recognized and interpreted by the associated electronics. As above, each of the stripes may be substantially identical in color to any underlying substrate and to each other and thus can be effectively indistinguishable to the naked eye as representing a code.

Example 6

Three Color Illumination

Figure 5:
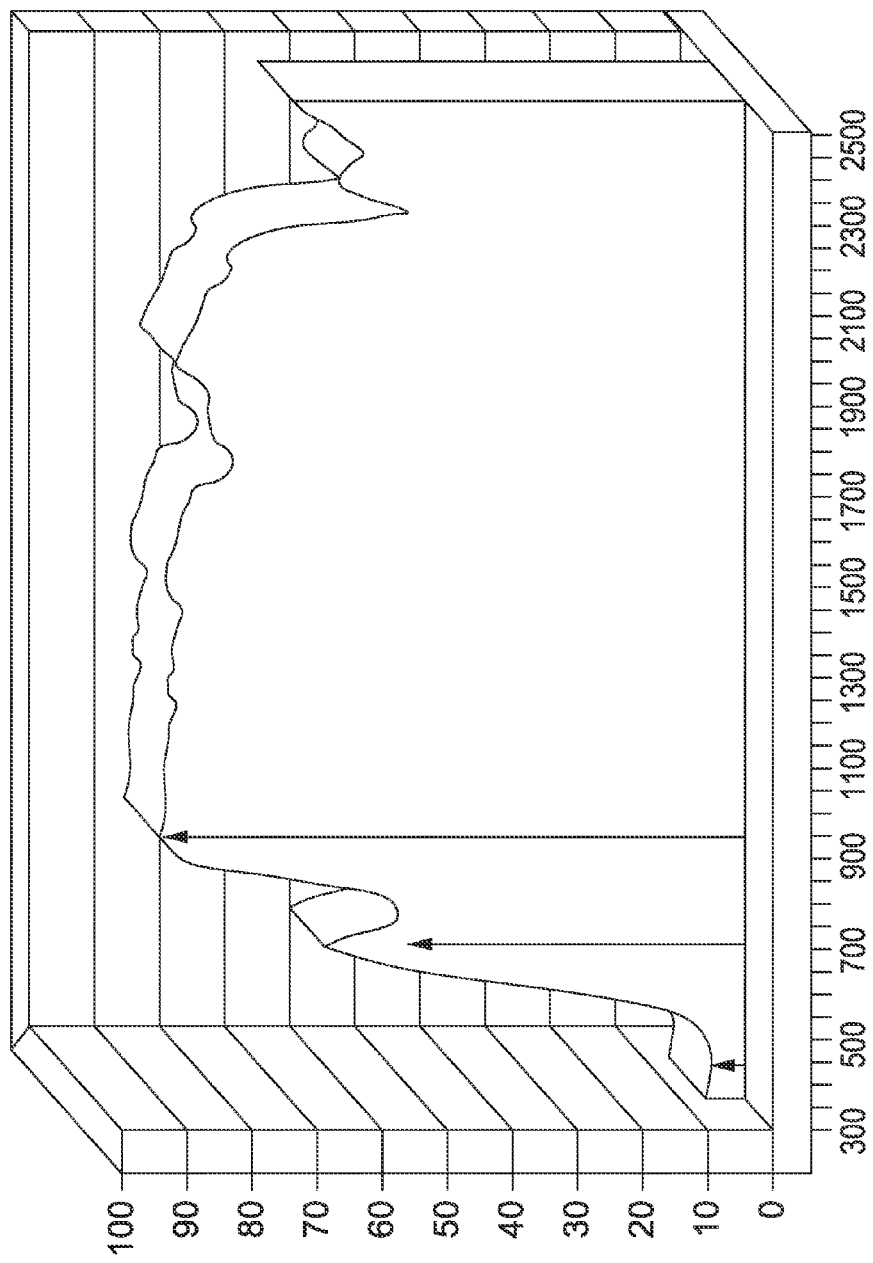

The potential for using a single paint (eg. Yellow 10P270) was examined for use with three different colored LEDs. In this case, the spectral profile of reflectivity of the paint could be used to monitor differential signal patterns from the various input wavelengths. As shown in FIG. 5, the reflective profile of the paint has a various peaks and valleys that can be "matched" to the input LED wavelengths such that ranges of input wavelengths can be utilized to establish reflectivity responses that provide expected absolute or differential signals. For example, for the reflective profile, input wavelengths of 400-470 nm will provide an expected 10% reflection response whereas a 690-700 nm and 940-950 nm input will provide an expected 60% and 90% reflection response respectively. As such, the absolute values and/or ratios of the responses can be compared to establish an authorized code signal.

Implementation Examples

Three-Color LED

A single three color LED may be utilized to effect a more complex code signal as described in relation to FIG. 5 in a more compact package. For example, three color (red, green, blue) LEDs can be configured to provide a sequenced and patterned output of different colored light along a common beam path. As such, the light can be readily directed against a common substrate requiring only a single receiver to receive the signal from each color. Moreover, more than one three-color LEDs may be paired with corresponding receivers and paints to generate additional reflectance codes that may be combined together to represent an authorized signal.

"Invisible" Bar Code

A bar code type system can be designed using a combination of paints having a substantially identical appearance to the naked eye but that provide a specific reflection response under specific illumination. In this case, as noted above, paints can be selected to substantially match the color of the underlying substrate/product such that the "code" is effectively not visible to the casual observer.

This implementation was tested in which a bar code was designed using two black paints (Black 30C591 (termed 0) and Black 20F944 (termed 1)) in which three alternating bands of each paint were painted on a substrate and illuminated with a 950 nm LED. That is, the bar code had the pattern 010101. The code was read by consecutive displacement of the bar code relative to the LED/sensor pair. The results showed a reflection pattern discernable as a corresponding "high" voltage signal x and "low" voltage signal y, i.e. xyxyxy.

In various embodiments of the bar code, the associate electronics can be designed in accordance with the physical characteristics of a product pair and/or the relative complexity of the code. That is, a bar code can be implemented utilizing a single LED/sensor pair in which the code is read by movement of LED/sensor pair relative to the code or where multiple LED/sensor pairs are oriented above each bar code element (i.e. color or stripe).

Importantly, it is understood that based on these principles, a wide range of signal patterns can be created that utilize various combinations of parameters of the LEDs, sensors, paints, physical orientation and movement of the elements, and size and shape of the substrate paints.

It is also understood that the associated electronics can be designed to provide various functions to a specific embodiments such as including power saving strategies that minimize or reduce power consumption through proximity switches and/or pulsed signals. In various embodiments, the system may also include one or more optical elements 61 that allow a single light source to be directed against different optical coatings as shown in FIG. 3A. In this case, the optical elements may be used to split the transmitter light to separate optical paths that are directed to the different optical coatings. Depending on the geometry and reception characteristics of the receiver, a single receiver may be utilized to receive reflected light from both optical coatings.

Product Pair Relationship

The physical relationship between a product pair will contribute to the type of code that may be implemented. Generally, the physical space that is available, the separation and/or the movement of one component relative to another may determine the specific design of keying system. Features such as proximity switches and pulsed powered may be utilized to minimize power consumption as understood by those skilled in the art.

Paints

In accordance with the invention, as described above, a number of different paints can be utilized to exploit the reflective properties of the paints. The ultimate selection of paints, as understood by those skilled in the art, will based on the desired keying application and consider a number of factors relevant to that application including but not limited to factors such as the level of desired security, the form and size of the substrate and the color of the substrate.

Paints can be applied to substrates using a variety of known production techniques.

LEDs

Factors used in selecting suitable LEDs include but are not limited to the spectral emission profile, the spatial dimensions (eg. Angular dimensions) of the emission profile, and the emission colors.

Photo Sensors

Photo sensors may be selected based on factors including but not limited to spectral sensitivity (e.g. Visible, near IR), the spatial dimensions of response, size (e.g. Profile size and dimensions) and speed. Photo sensors can include photodiodes, phototransistors and light-to-voltage converters.

Although the present invention has been described and illustrated with respect to preferred embodiments and preferred uses thereof, it is not to be so limited since modifications and changes can be made therein which are within the full, intended scope of the invention as understood by those skilled in the art.

What is claimed is:

1. A keying system for interpreting a code based on a spectral response of at least two optical coatings on a substrate between at least one optical transmitter and at least one receiver while authorizing pairing of a first product with a second product to allow or prevent dispensing of the second product by the first product, the system comprising:
   a transmitter located on the first product, the transmitter configured to transmit at least a first light signal against first and second optical coatings of the code located on the second product when the first product and the second product are being paired, wherein the first product is a dispenser and the second product is a consumable product;
   a receiver operatively located on the first product, the receiver configured to receive reflected light by the first and second optical coatings of the code;
   an optical splitter positioned adjacent the transmitter and configured to split the first light signal to separate optical paths that are directed to the first and second optical coatings; and
   receiver electronics operatively connected to the receiver and configured to:
      interpret reflected light received at the receiver against an authorized signal by analysis of the spectral response including analysis of the degree of absorption and/or reflection of the reflected light at the first and second optical coatings, to thereby determine whether the reflected light received at the receiver matches the authorized signal;
      in response to determining that the reflected light received at the receiver matches the authorized signal, authorize pairing of the second product with the first product to allow the dispensing of the second product by the first product; and
      in response to determining that reflected light received at the receiver does not match the authorized signal, prevent pairing of the second product with the first product to prevent the dispensing of the second product by the first product.

2. The keying system of claim 1, wherein the transmitter is an LED light source.

3. The keying system of claim 2, wherein the LED is a multi-color LED enabling sequenced generation of at least two wavelengths within the LED and wherein the receiver receives a corresponding absorption and/or reflected signal of the at least two wavelengths.

4. The keying system of claim 1, wherein the system includes at least two transmitters located on the first product and each transmitter transmits a different wavelength of light against the first and second optical coatings.

5. The keying system of claim 1, wherein each of the first and second optical coatings is paired with a corresponding transmitter and receiver pair.

6. The keying system of claim 5, wherein each transmitter of each transmitter and receiver pair emits different wavelength light.

7. The keying system of claim 6, wherein the first and second optical coatings have different absorption and/or reflection properties.

8. The keying system as in claim 5, wherein the first and second optical coatings have different absorption and/or reflective properties.

9. The keying system of claim 1, wherein the first and second optical coatings have different absorption and/or reflection properties.

10. The keying system of claim 1, wherein one or both of the first and second optical coatings is on a rotating substrate and at least one of the first and second optical coatings rotates past a reflection point of the transmitter and receiver pair on the substrate.

11. The keying system of claim 10, wherein the rotating substrate includes both of the first and second optical coatings, and the first and second optical coatings have different absorption and/or reflection properties.

12. The keying system of claim 11, wherein the first and second optical coatings are painted stripes.

13. The keying system of claim 12, wherein the first and second optical coatings have substantially the same color and different absorption and/or reflection properties.

14. The keying system of claim 1, wherein the first light signal is pulsed.

15. The keying system of claim 1, wherein the consumable product is a cartridge.

16. The keying system of claim 1, wherein the analysis of the spectral response includes analysis of one or more of:
   an absolute value of a degree of absorption;
   an absolute value of a degree of reflection;
   a ratio between degrees of absorption;
   a ratio between degrees of reflection; and
   a ratio between a degree of absorption and a degree of reflection.

17. The keying system of claim 1, wherein the first product and second product are stationary with respect to one another during pairing.

18. The keying system of claim 1, wherein the code comprises a single paint.

19. The keying system of claim 1, wherein the code comprises pigments configured to match a color of the substrate or product such that, to the naked eye, the code is not distinguishable from the substrate or product.

20. A keying system for interpreting a code based on a spectral response of at least two optical coatings on a substrate while pairing a first product with a second product to allow or prevent dispensing of the second product with the first product, the system comprising:
   at least one transmitter and receiver pair including a transmitter and a receiver, both located on the first product, the transmitter configured to transmit a light signal against first and second optical coatings located on the second product, wherein the first product is a dispenser and the second product is a consumable product,
   an optical splitter positioned adjacent the transmitter and configured to split the light signal to separate optical paths that are directed to the first and second optical coatings, and
   receiver electronics operatively connected to the receiver configured to:
      interpret reflected light at the receiver against an authorized signal by analysis of the degree of absorption and/or reflection of the reflected light at the first and second optical coatings, to thereby determine whether the reflected light received at the receiver matches the authorized signal;
      in response to determining that the reflected light received at the receiver matches the authorized signal, authorize pairing of the second product with the first product to allow the dispensing of the second product by the first product; and
      in response to determining that reflected light received at the receiver does not match the authorized signal, prevent pairing of the second product with the first product to prevent the dispensing of the second product by the first product.

21. A method of pairing a first product with a second product to allow or prevent dispensing of the second product with the first product, the method comprising the steps of:
   a) positioning the first product with the second product, wherein the first product is a dispenser and has a transmitter and a receiver, and the second product is a consumable product and has a code comprising first and second optical coatings;
   b) transmitting a first light signal from the transmitter against the first and second optical coatings;
   c) splitting the first light signal to separate optical paths that are directed to the first and second optical coatings;
   d) receiving a reflected light signal at the receiver from light reflected off the first and second optical coatings; and
   e) comparing the reflected light signal to a pre-determined signal pattern by spectral analysis of the degree of absorption and/or reflection of the reflected light at the one or more optical coatings, to thereby determine whether the reflected light received at the receiver matches an authorized signal;
   f) in response to determining that the reflected light received at the receiver matches the authorized signal, authorize pairing of the second product with the first product to allow the dispensing of the second product by the first product; and
   g) in response to determining that reflected light received at the receiver does not match the authorized signal, prevent pairing of the second product with the first product to prevent the dispensing of the second product by the first product.

22. The method of claim 21, wherein step d) includes receiving at least a second light signal.

23. The method of claim 21, wherein the first and second optical coatings of the second product include at least two optical coatings and wherein each of the first and second optical coatings is paired with a corresponding transmitter and receiver pair such that steps a)-c) include positioning, transmitting and receiving across corresponding transmitter and receiver pairs.

24. The method of claim 23, wherein the first and second optical coatings have different reflection properties.

* * * * *